(12) United States Patent
Manetsch et al.

(10) Patent No.: US 11,479,532 B2
(45) Date of Patent: Oct. 25, 2022

(54) 5-AMINOLEVULINATE SYNTHASE INHIBITORS AND METHODS OF USE THEREOF

(71) Applicant: UNIVERSITY OF SOUTH FLORIDA, Tampa, FL (US)

(72) Inventors: Roman Manetsch, Boston, MA (US); Gloria C. Ferreira, Tampa, FL (US); Bosko M. Stojanovski, St. Louis, MO (US); Katya Pavlova Nacheva, Holiday, FL (US)

(73) Assignee: University of South Florida, Tampa, FL (US)

( * ) Notice: Subject to any disclaimer, the term of this patent is extended or adjusted under 35 U.S.C. 154(b) by 209 days.

(21) Appl. No.: 16/625,363

(22) PCT Filed: Jun. 21, 2018

(86) PCT No.: PCT/US2018/038790
§ 371 (c)(1),
(2) Date: Dec. 20, 2019

(87) PCT Pub. No.: WO2018/237163
PCT Pub. Date: Dec. 27, 2018

(65) Prior Publication Data
US 2021/0269397 A1 Sep. 2, 2021

Related U.S. Application Data

(60) Provisional application No. 62/524,341, filed on Jun. 23, 2017.

(51) Int. Cl.
*C07C 311/51* (2006.01)
*C07D 209/12* (2006.01)
(Continued)

(52) U.S. Cl.
CPC .......... *C07D 209/12* (2013.01); *C07C 311/51* (2013.01); *C07D 207/444* (2013.01); *C07D 211/14* (2013.01)

(58) Field of Classification Search
CPC ... C07C 311/19; C07C 311/51; C07D 207/08; C07D 207/36; A61K 31/18
See application file for complete search history.

(56) References Cited

U.S. PATENT DOCUMENTS 7,183,320 B2 * 2/2007 Shih ..................... C07D 249/08
514/617
2004/0147581 A1 7/2004 Taylor et al.
(Continued)

FOREIGN PATENT DOCUMENTS

WO WO-2007/026028 A2 3/2007

OTHER PUBLICATIONS

International Search Report in International Application No. PCT/US2018/038790, filed Jun. 21, 2018.
(Continued)

*Primary Examiner* — Johann R Richter
*Assistant Examiner* — Danielle Sullivan
(74) *Attorney, Agent, or Firm* — Quarles & Brady LLP

(57) ABSTRACT

Disclosed herein, are 5-Aminolevulinate synthase inhibitors and methods for their use in the treatment of *porphyria*. In at least one specific embodiment, the 5-Aminolevulinate synthase inhibitors can include compounds or salts thereof of Formulas (I-V)

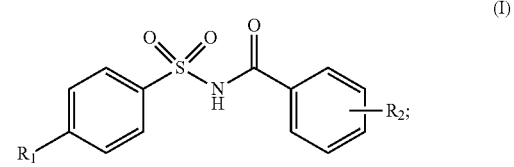

(I)

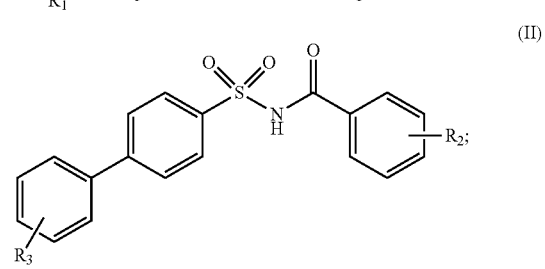

(II)

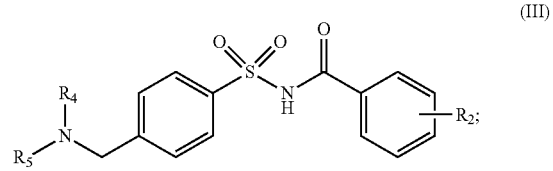

(III)

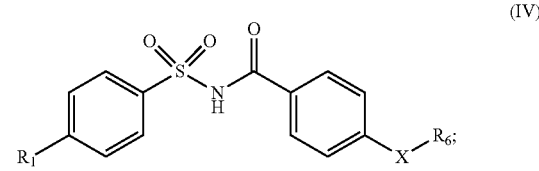

(IV)

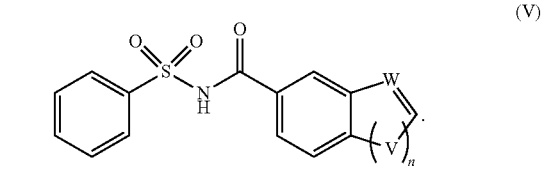

(V)

4 Claims, No Drawings

(51) Int. Cl.
    *C07D 207/444*     (2006.01)
    *C07D 211/14*     (2006.01)

(56) References Cited

U.S. PATENT DOCUMENTS

| | | | |
|---|---|---|---|
| 2013/0281511 A1* | 10/2013 | Bettencourt | A61P 25/20 |
| | | | 514/44 A |
| 2016/0022642 A1 | 1/2016 | Crews et al. | |
| 2016/0031858 A1 | 2/2016 | Nebolsin et al. | |
| 2016/0116482 A1* | 4/2016 | Manetsch | A61K 31/427 |
| | | | 506/9 |

OTHER PUBLICATIONS

Fratz, E. J. et al., "Toward Heme: 5-Aminolevulinate Synthase and Initiation of Porphyrin Synthesis," *Handbook of Porphyrin Science*, pp. 1-79.

Hu, X. et al., "Kinetic target-guided synthesis†," *Chemical Society Reviews*, 2010, 39:1316-1324, abstract only.

Hu, X. et al., "Bcl-$X_L$-Templated Assembly of Its Own Protein-Protein Interaction Modulator from Fragments Decorated with Thio Acids and Sulfonyl Azides," *J. Am. Chem. Soc.*, 2008,130:13820-13821, American Chemical Society.

Matthew, M. et al., "Aminomalonate as an Enzyme Inhibitor," *Biohem. J.*, 1963, 87:601-612.

Sharpless, K. B. et al., "In situ click chemistry: a powerful means for lead discovery," *Expert Opinion on Drug Discovery*, 2006, 1(6):525-538, abstract only.

Stojanovski, B. M. et al., "Catalytically active alkaline molten globular enzyme: Effect of pH and temperature on the structural integrity of 5-aminolevulinate synthase*," *Biochim Biophys Acta.*, Dec. 2014, 1544(12):2145-2154.

\* cited by examiner

5-AMINOLEVULINATE SYNTHASE INHIBITORS AND METHODS OF USE THEREOF

CROSS-REFERENCE TO RELATED APPLICATION

This application is the U.S. national stage application of International Patent Application No. PCT/US2018/038790, filed Jun. 21, 2018; which claims the benefit of U.S. Provisional Patent Application Ser. No. 62/524,341, filed Jun. 23, 2017, the disclosure of each of which is hereby incorporated by reference in its entirety, including any figures, tables, or drawings.

BACKGROUND OF THE INVENTION

5-Aminolevulinate synthase (ALAS) is the first enzyme and a regulatory enzyme of the heme biosynthetic pathway in metazoan [1]. ALAS is, therefore, a logical target for reducing porphyrin accumulation characteristic of *porphyria* [2], which can be found in certain hepatic and erythropoietic/blood disorders. Up to now, aminomalonate remains the only known inhibitor of ALAS ($IC_{50}$=7 µM) [3]. New compounds are needed to combat *porphyria* due to the limited number of 5-Aminolevulinate synthase inhibitors.

BRIEF SUMMARY OF THE INVENTION

Provided herein are new compounds and methods of using the same in the treatment *porphyria*. In at least one specific embodiment, the compound or a salt thereof, can include compounds of Formulas (I-V):

Formula (I)
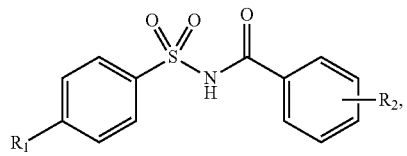

Formula (II)
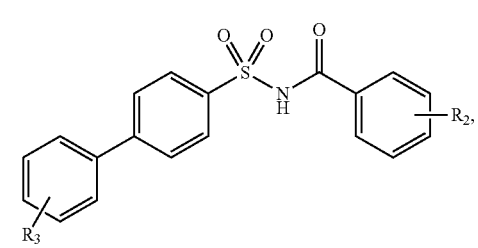

Formula (III)
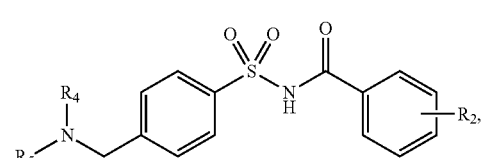

Formula (IV)
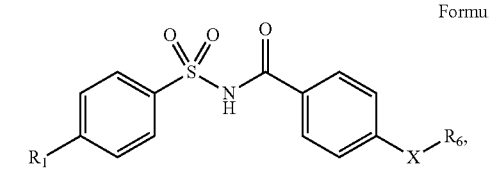

Formula (V)
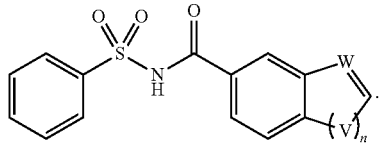

In another specific embodiment, the method can include administering a composition that includes one or more compounds of Formulas (I-V).

DETAILED DISCLOSURE OF THE INVENTION

A kinetic target-guided synthesis (TGS) approach against 5-aminolevulinate synthase (ALAS) was developed, which allows high-throughput screening and identification of novel ALAS-specific inhibitors. A sulfo-click reaction was used in the kinetic TGS screening to identify ALAS inhibitors, thus allowing multi-fragment screening with a rapid throughput.

Target-guided synthesis is a fragment-based approach that combines the syntheses with screening of libraries of low molecular weight compounds in a single step [4,5]. In TGS, the target protein (e.g., ALAS) is actively involved in the assembly of its own bidentate ligand from a pool of smaller reactive fragments [6]. An expanded library of fragments was used that covers a larger chemical space allowing exploration of multi-fragment screening. Fragments comprising sulfonyl azide or thio acid groups (sulfonyl azides SZ1-SZ38 and thio acids TA1-TA45) are identified and synthesized for ALAS.

ALA inhibitors according to embodiments of the invention include the compounds of Formulas (I-V):

Formula (I)
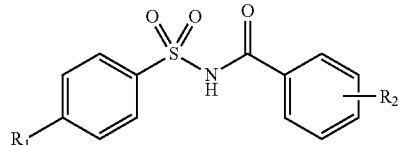

Formula (II)
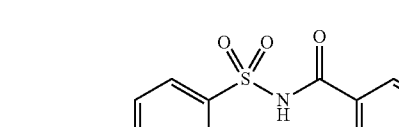

Formula (III)

Formula (IV)
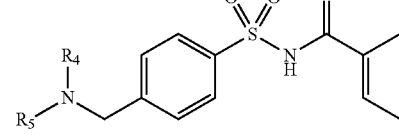

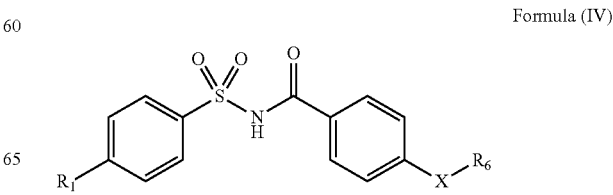

-continued

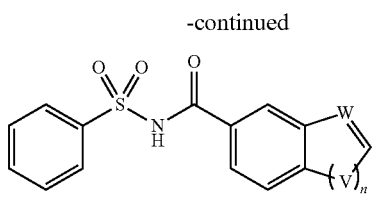

Formula (V)

where $R_1$, $R_2$, $R_3$, $R_4$, $R_5$, $R_6$ is independently selected from the group consisting of H; F; Cl; Br; I; OH; $C_{1-14}$ linear, branched, or cyclic alkyl, including, but not limited, to methyl, ethyl, n-propyl, isopropyl, n-butyl, sec-butyl, isobutyl, tert-butyl, cyclopropyl, cyclobutyl, cyclopentyl, or cyclohexyl; $C_{2-14}$ linear, branched, or cyclic alkenyl, including, but not limited to ethenyl, propenyl, butenyl, butadienyl, cyclopentenyl, methylcycpentenyl, dimethylcyclohexyl, where one or more double bond is located at any position in the alkenyl carbon chain in an E or Z conformation and where a plurality of double bonds are isolated or conjugated; $C_{2-14}$ linear, branched, or cyclic alkynyl, where the one or more triple bond is located at any position in the alkynyl carbon chain; —OR, where R is $C_{1-14}$ alkyl or $C_{2-14}$ alkenyl; $C_{6-14}$ aryl; $C_{7-28}$ aralkyl; $C_{7-28}$ alkaryl; heteroaryl, halogenated alkyl; heterocyclyl; amino; alkylamino; arylamino; dialkylamino, where the alkyls are independently $C_{1-14}$ alkyl; alkylarylamino; diarylamino; tetraalkylammonium, where the alkyls are independently $C_{1-14}$ alkyl; aryltrialkylammonium, where the alkyls are independently $C_{1-14}$ alkyl; diaryldialkylammonium, where the alkyls are independently $C_{1-14}$ alkyl and the aryls are independently $C_{6-14}$ aryl; acylamino; hydroxyl; alkoxy; aryloxy; arylalkoxy; acyloxy; nitro; carbamoyl; trifluoromethyl; phenoxy; benzyloxy; alkaryl; arylalkyl; carbamate; hydroxyalkyl; aminoalkyl; alkoxyalkyl; hydroxyalkyl; aminoalkyl; alkoxyalkyl; alkyltriphenylphosphonium; —C(O)R, where R is $C_{1-14}$ alkyl or $C_{2-14}$ alkenyl; —C(O)H; —C(O)OH; —OC(O)R where R is $C_{1-14}$ alkyl or $C_{2-14}$ alkenyl; —ROC(O)R' where R and R' are independently $C_{1-14}$ alkyl or $C_{2-14}$ alkenyl; —RC(O)OR', where R is $C_{1-14}$ alkylene, $C_{2-14}$ alkenylene, or arylene and R' is $C_{1-14}$ alkyl, $C_{2-14}$ alkenyl, or aryl; —C(O)OR where R is $C_{1-14}$ alkyl, $C_{2-14}$ alkenyl, or aryl; —OCOOR, where R is $C_{1-14}$ alkyl, $C_{2-14}$ alkenyl, or aryl; —C(O)NRR' where R and R' are independently H, $C_{1-14}$ alkyl, $C_{2-14}$ alkenyl, or aryl; —N(R)C(O)R', where R is $C_{1-14}$ alkyl, $C_{2-14}$ alkenyl, or aryl; —N(C(O)R)(C(O)R'), where R and R' are independently $C_{1-14}$ alkyl, $C_{2-14}$ alkenyl, or aryl or R and R' are combined as $C_{1-14}$ alkylene, $C_{2-14}$ alkenylene, or arylene; —OCN; —NCO; —ONO$_2$; —CN; —NC; —NO; —CH=NOH; —B(OH)$_2$; —B(OR)(R'), where R where R and R' are independently H, $C_{1-14}$ alkyl, or $C_{2-14}$ alkenyl; —B(OR)(OR'), are independently H, $C_{1-14}$ alkyl, or $C_{2-14}$ alkenyl; —PR$_2$, where R is independently selected from H, $C_{1-14}$ alkyl, or $C_{2-14}$ alkenyl; —OP(O)(OR)$_2$, where R is independently selected from H, $C_{1-14}$ alkyl, or $C_{2-14}$ alkenyl; —P(O)(R)(OH), where R is selected from $C_{1-14}$ alkyl or $C_{2-14}$ alkenyl; —SH; thioalkyl; —SR, where R is selected from $C_{1-14}$ alkyl or $C_{2-14}$ alkenyl; —SSR, where R is $C_{1-14}$ alkyl or $C_{2-14}$ alkenyl; sulfonamide; —S(O)R, where R is $C_{1-14}$ alkyl or $C_{2-14}$ alkenyl; —SO$_2$H; —SO$_3$H; thiocyanate; isothiocyanate; —C(S)R where R is $C_{1-14}$ alkyl or $C_{2-14}$ alkenyl; where X is O, N, or S; where V is —CH$_2$—, CO, S, and NR$_7$, where R$_7$ is independently H; $C_{1-14}$ alkyl; $C_{2-14}$ alkenyl; heteroalkyl; or heteroaryl;

where n is an integer from 1 to 4; and where W is —CH$_2$—, O, S and NR$_8$, where R$_8$ is selected from H; $(C_{1-14})$alkyl, such as methyl, ethyl, n-propyl, isopropyl, n-butyl, sec-butyl, isobutyl, tert-butyl; $(C_{2-14})$alkenyl, such as ethenyl, propenyl, butenyl, where the double bond can be located at any position in the alkenyl carbon chain, including any alkenyl conformational isomers; heteroalkyl; and heteroaryl.

As used herein, the term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms. The term "alkyl" can include both "unsubstituted alkyls" and "substituted alkyls," the latter of which refers to alkyl moieties having one or more substituents replacing hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls or cyclic alkyls can be substituted in the same manner.

As used herein, "heterocycl" can refer to a non-aromatic ring and having the specified number of member atoms being saturated or having one or more degrees of unsaturation and, unless otherwise specified, containing one or more heteroatoms. Suitable heteroatoms include, but are not limited to, O, N, Si, P, Se, B, and S, where the phosphorous and sulfur atoms are optionally oxidized, and the nitrogen heteroatom is optionally quaternized.

As used herein, "heteroaryl" can refer to an aromatic ring having the specified number of member atoms and, unless otherwise specified, containing one or more heteroatoms. Suitable heteroatoms include, but are not limited to, O, N, Si, P, Se, B, and S, where the phosphorous and sulfur atoms are optionally oxidized, and the nitrogen heteroatom is optionally quaternized. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, where the phosphorous and sulfur atoms are optionally oxidized, and the nitrogen heteroatom is optionally quaternized.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, where the phosphorous and sulfur atoms are optionally oxidized, and the nitrogen heteroatom is optionally quaternized.

As used herein, "alkoxyl" or "alkoxy" can refer to an alkyl group having an oxygen radical attached thereto.

Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy" can include —O-aryl and O-heteroaryl.

As used herein, "amine" or "amino" (and its protonated form) can include both unsubstituted and substituted amines, and "ammonium" e.g., a moiety that can be represented by the general formula:

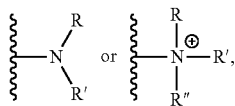

respectively,
where R, R', and R" each independently represent a hydrogen, an alkyl, an alkenyl, an aryl, —(CH$_2$)$_m$—R$_C$, or where R and R' are taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero to 8.

As used herein, "amide" is —C(=O)NRR' or —N(R)C(=O)R' where: R and R' can include a hydrogen, alkyl, cycloalkyl, alkenyl, cycloalkenyl, alkynyl, or aryl; or R and R' are combined as an alkylene, alkenylene, or arylene to form a ring including the nitrogen. As used herein, "imide" is —N(C(=O)R)(C(=R')) where: R and R' can include a hydrogen, alkyl, cycloalkyl, alkenyl, cycloalkenyl, alkynyl, or aryl; or R and R' are combined as an alkylene, alkenylene, or arylene to form a ring including the nitrogen.

As used herein, "amido" can include an amino-substituted carbonyl represented by the general formula:

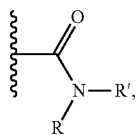

where R and R' can include a hydrogen, alkyl, cycloalkyl, alkenyl, cycloalkenyl, or alkynyl; or R and R' are combined as an alkylene, alkenylene, or arylene to form a ring including the nitrogen.

As used herein, "aryl" can include a C$_6$-C$_{14}$-membered aromatic, fused aromatic, fused heterocyclic, or biaromatic, or bihetereocyclic ring systems. Examples include: phenyl and napthyl groups. The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

As used herein, "heteroaryl", "aryl heterocycles" or "heteroaromatics" can include a C$_3$-C$_{14}$ aromatic ring including one or more heteroatoms, includes 5-, 6-, 7-, 8-, 9-, and 10-membered single-ring aromatic groups that may include one to four heteroatoms, for example, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions, such as a halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, and —CN.

As used herein, "aralkyl," can include an alkyl group substituted with an aryl group (e.g., an aromatic or heteroaromatic group).

As used herein, "aralkyloxy" can include —O-aralkyl.

As used herein, "carbocycle," can include an aromatic or non-aromatic ring(s) in which each atom of the ring(s) is carbon.

The term "carbonyl" can be represented by C=O comprising groups of the general formula:

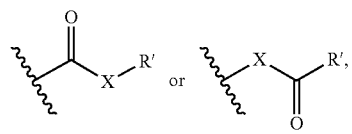

where X is a bond or represents an oxygen or a sulfur, and R and R' can include a hydrogen, alkyl, cycloalkyl, alkenyl, cycloalkenyl, alkynyl, or aryl. Where X is an oxygen and R or R' is not hydrogen, the formula represents an "ester." Where X is oxygen, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" can include any element other than carbon or hydrogen. Exemplary heteroatoms include, but are not limited to, boron, nitrogen, oxygen, phosphorus, sulfur, silicon, arsenic, and selenium.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g., 1-14 carbon atoms, and optionally can include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

Specific compounds of Formulas (I-V) can include, but are not limited to:

SZ10TA40

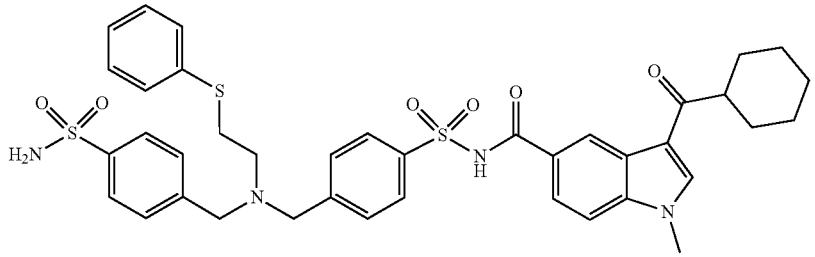

SZ11TA40

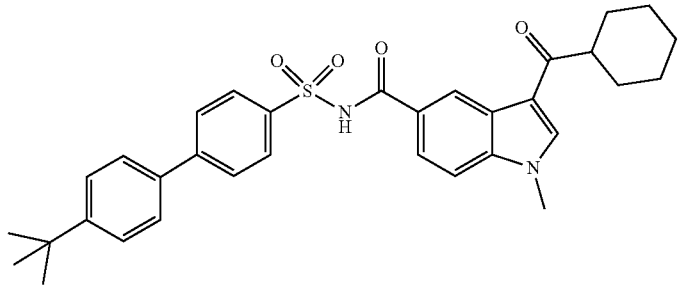

SZ12TA42

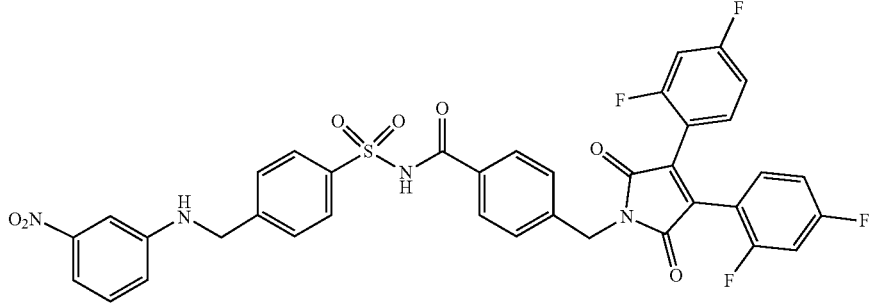

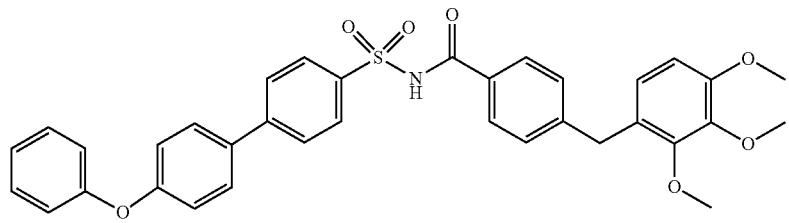

SZ35TA24

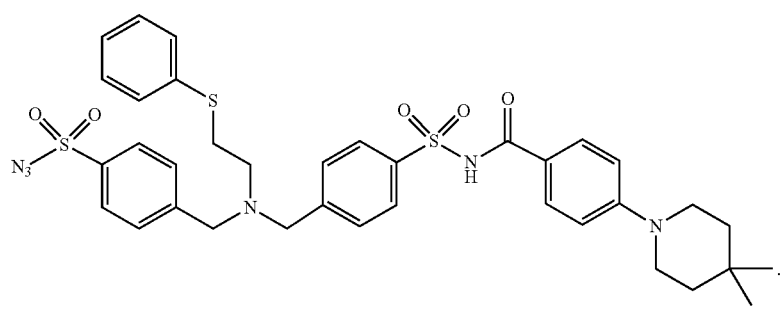

SZ10TA2

The method of treating *porphyria*, according to embodiments of the invention, can include, but is not limited to, administering one or more compounds of Formulas (I-V) or a composition of one or more compounds of Formulas (I-V). The administration can include, but is not limited to: administration though oral pathways, which administration includes administration in capsule, tablet, granule, spray, syrup, or other such forms; administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as administration topically; and administration via controlled released formulations, depot formulations, and infusion pump delivery. As further examples of such modes of administration and as further disclosure of modes of administration, disclosed herein are various methods for administration of the disclosed compounds and pharmaceutical compositions including modes of administration through intraocular, intranasal, and intra-auricular pathways.

In embodiments of the invention, the method is characterized by the use of the compounds of Formulas (I-V) alone or in any combination, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods can also be applied to testing chemical activity in vivo.

In embodiments of the invention, the compounds of Formulas (I-V) can be in the form of pharmaceutically acceptable salts. The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

The composition containing compounds of Formulas (I-V) can include, but is not limited to, a pharmaceutically acceptable carrier. The term "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

Determining a therapeutically effective amount of the composition is well within the capability of those skilled in the art. A "therapeutically effective amount" means that amount of the compound in the composition which, when administered to a human suffering from a *porphyria*, is sufficient to effect treatment for the *porphyria*.

The amount of compounds which are administered and the dosage regimen for treating a *porphyria* with the compounds of Formulas (I-V) and/or compositions depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose can include about 0.01 to 500 mg/kg, about 0.01 and about 50 mg/kg, or about 0.01 and about 30 mg/kg of body weight may be appropriate. The daily dose can be administered in one to four doses per day.

MATERIALS AND METHODS

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Synthesis of Selected Thio Ester and Sulfonyl Azide Intermediates Synthesis of SZ10

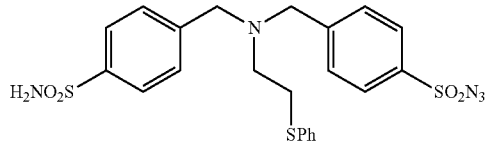

SZ10

4-(((2-(Phenylthio)ethyl)(4-sulfamoylbenzyl)amino) methyl)benzenesulfonyl azide (SZ10) was prepared according to the article, *ACS Chem. Biol.* (2011), 6, 724-732, which is hereby incorporated by reference in its entirety.

Synthesis of SZ11

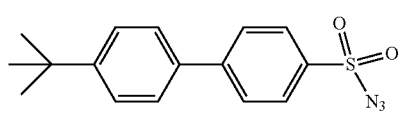

SZ11

4'-(Tert-butyl)-[1,1'-biphenyl]-4-sulfonyl azide (SZ11) was prepared according to the article, Chem. Comm. (2012), 48, 1526-1528, which is hereby incorporated by reference in its entirety.

Synthesis of SZ12

SZ12 was synthesized by the reaction scheme:

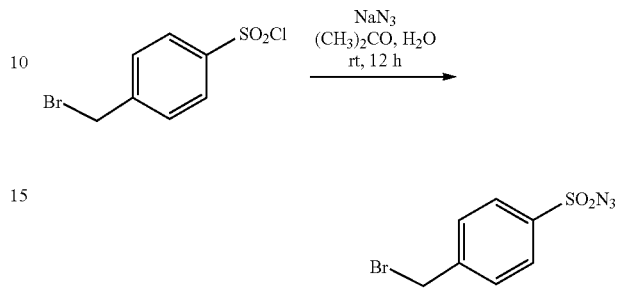

The starting material, 4-(bromomethyl)benzenesulfonyl azide, was prepared according to the article, Hu, X. D., Sun, J., Wang, H.-G., Manetsch, R. Bcl-$X_L$-templated Assembly of Its Own Protein-Protein Interaction Modulator from Fragments Decorated with Thio Acids and Sulfonyl Azides. *J. Am. Chem. Soc.* 130, 13820-13821 (2008), which is hereby incorporated by reference in its entirety. SZ12 was synthesized by the reaction:

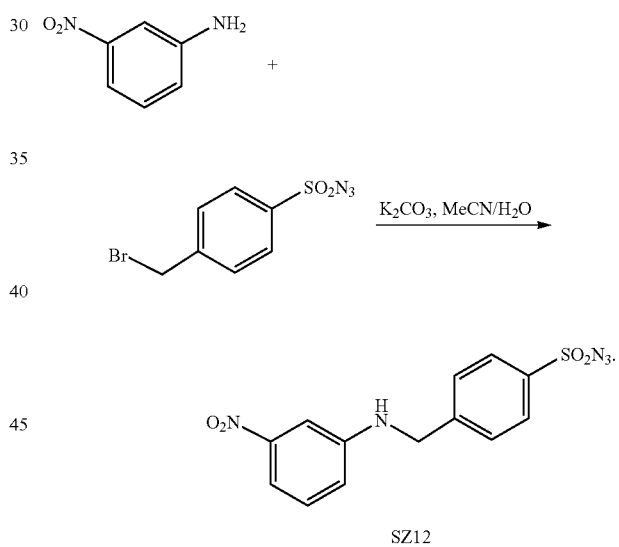

SZ12

To a round bottom flask was charged with 3-nitroaniline (138 mg, 1.00 mmol), 4-(bromomethyl)benzenesulfonyl azide (275 mg, 1.00 mmol), $K_2CO_3$ (276 mg, 2.00 mmol), MeOH/$H_2O$ (9:1, 12.5 mL), a magnetic stir bar and stirred at rt for 12 h. The reaction was judged to be complete via TLC, quenched with water, extracted with EtOAc, dried over $Na_2SO_4$ and concentrated under reduced pressure. The crude residue was purified using flash column chromatography and 4-(((3-nitrophenyl)amino)methyl)benzenesulfonyl azide SZ12 was obtained in 67% yield. $R_f$=0.35 in hexanes: EtOAc=3:1. $^1$H NMR (600 MHz, CDCl$_3$) δ 7.94 (d, J=8.3 Hz, 2H), 7.61 (d, J=8.2 Hz, 2H), 7.57 (dd, J=8.1, 1.8 Hz, 1H), 7.40 (t, J=2.1 Hz, 1H), 7.30 (t, J=8.2 Hz, 1H), 6.86 (dd, J=8.2, 2.2 Hz, 1H), 4.64 (s, 1H), 4.56 (s, 2H). $^{13}$C NMR (101 MHz, CDCl$_3$) δ: 148.2, 146.4, 130.2, 128.4, 128.3, 128.2, 127.8, 118.9, 113.0, 106.9, 47.5. HRMS (ESI) calcd for $C_{13}H_{11}N_5O_4S$ [M+K]$^+$: 372.0163, found: 372.0145.

Synthesis of SZ35

SZ35 was synthesized by the reaction:

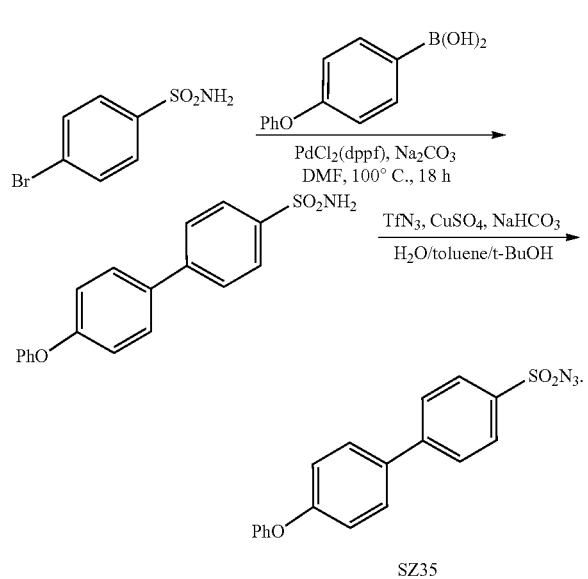

To a flame dried sealed tube was charged with 4-bromobenzenesulfonamide (250 mg, 1.06 mmol), (4-phenoxyphenyl)boronic acid (250 mg, 1.17 mmol), PdCl$_2$(dppf) (70.0 mg, 8.0 mol %), 2 N Na$_2$CO$_3$ (0.75 mL, 3.18 mmol), DMF (8.5 mL), a magnetic stir bar and purged with argon. The reaction was heated at 100° C. for 18 h. The reaction mixture was cooled, diluted with CH$_2$Cl$_2$ and filtered through Celite. The solution was dried over Na$_2$SO$_4$ and the solvent evaporated under reduced pressure. The aryl ether sulfonamide intermediate was purified using flash column chromatography resulting in a yellowish solid (310 mg, 90%). $R_f$=0.56 in hexanes:EtOAc=1:1. $^1$H NMR (400 MHz, DMSO-d$_6$) δ 7.98-7.81 (m, 4H), 7.81-7.68 (m, 2H), 7.51-7.36 (m, 4H), 7.19 (t, J=7.4 Hz, 1H), 7.10 (t, J=8.9 Hz, 4H). $^{13}$C NMR (101 MHz, DMSO-d$_6$) δ 157.19, 156.14, 142.59, 133.61, 130.10, 128.66, 126.75, 126.25, 123.83, 119.02, 118.74, 95.79.

An Erlenmeyer flask was charged with aryl ether sulfonamide intermediate (310 mg, 0.95 mmol), NaHCO$_3$ (320 mg, 3.81 mmol), water (1.1 mL), 1 M CuSO$_4$ (0.04 mL of a 1 M solution, 4 mol %), a magnetic stir bar and stirred at rt. To the flask a freshly prepared solution of TfN$_3$ (1.9 mL of a 0.75 M solution, 1.50 mmol) in toluene followed by t-BuOH (7.6 mL) was added and stirred behind a blast shield for 18 h. The reaction mass was transferred to a round bottom flask and diluted with xylenes. Volatile solvents were removed under reduced pressure, the product precipitated and the solids recovered using vacuum filtration. The crude residue was purified using flash column chromatography and 4'-phenoxy-[1,1'-biphenyl]-4-sulfonyl azide SZ35 was obtained as a yellow solid (234 mg, 70%).%). $R_f$=0.86 in hexanes:EtOAc=1:1. $^1$H NMR (400 MHz, CDCl$_3$) δ 8.02 (d, J=8.2 Hz, 2H), 7.82-7.76 (m, 2H), 7.63-7.58 (m, 2H), 7.44-7.37 (m, 2H), 7.22-7.16 (m, 1H), 7.15-7.08 (m, 4H). $^{13}$C NMR (101 MHz, CDCl$_3$) δ 158.6, 156.3, 147.1, 136.5, 133.2, 129.9, 128.8, 128.1, 127.8, 124.0, 119.5, 118.9. HRMS (ESI) calcd for C$_{18}$H$_{13}$N$_3$O$_3$S [M+H]$^+$: 352.0751, found: 352.0757.

Synthesis of TE2

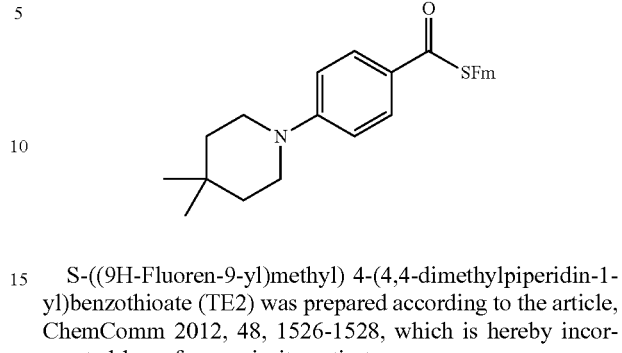

S-((9H-Fluoren-9-yl)methyl) 4-(4,4-dimethylpiperidin-1-yl)benzothioate (TE2) was prepared according to the article, ChemComm 2012, 48, 1526-1528, which is hereby incorporated by reference in its entirety.

Synthesis of TE24

TE24 was synthesized by the reaction scheme:

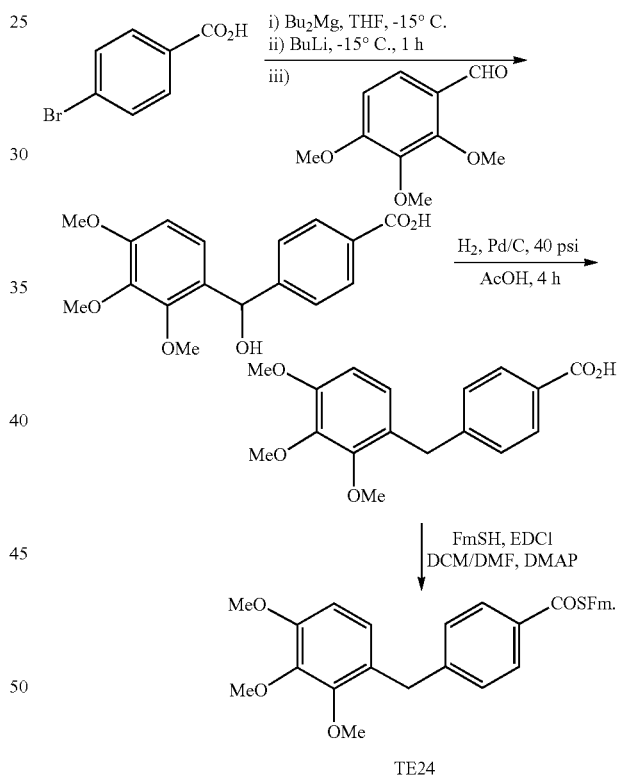

To a flame dried flask was charged with 4-bromobenzoic acid (1.00 g, 4.97 mmol), THF (5 mL), a magnetic stir bar, purged with argon and cooled to −15° C. A 1.0 M solution of dibutylmagnesium in heptane (2.58 mL, 2.59 mmol) was added dropwise followed by the addition of a 2.5 M solution of n-butyllithium (2.20 mL, 5.32 mmol) over the course of 20 min and stirred for 1 h. A solution of 2,3,4-trimethoxybenzaldehyde (1.95 g, 4.97 mmol) in THF (2 mL) was added and stirred for 1 h. The resulting reaction mixture was quenched with 1 M HCl, allowed to come to rt and stirred overnight. The resulting solution containing benzyl alcohol intermediate was extracted with EtOAc, dried with Na$_2$SO$_4$, concentrated under reduced pressure and purified using flash column chromatography. Catalytic hydrogenation of benzylic alcohol intermediate was performed by dissolving the residue in AcOH, adding the solution to a Parr hydrogenator pressure bottle along with Pd/C. The pressure bottle was purged with hydrogen gas three times, charged with a hydrogen atmosphere to 40 psi and shaken for 4 h. The reaction was judged to be complete via TLC analysis. The reaction mass was then filtered through Celite, washed with MeOH, concentrated under reduced pressure and crude carboxylic acid was purified using flash column chromatography. $^1$H NMR (400 MHz, CDCl$_3$) δ 8.02 (d, J=6.3 Hz, 2H), 7.30 (d, J=6.6 Hz, 2H), 6.81 (d, J=7.4 Hz, 1H), 6.62 (d, J=7.4 Hz, 1H), 3.99 (br. s., 2H), 3.89-3.80 (m, 6H), 3.73 (br. s., 3H).

The carboxylic acid was transformed into TE24 as previously reported in ACS Chem Biol 2011, 6, 724-732. The three synthetic steps gave TE24 with a 25% overall yield. $^1$H NMR (400 MHz, CDCl$_3$) δ 7.90-7.86 (m, 2H), 7.76 (t, J=6.4 Hz, 4H), 7.44-7.38 (m, 2H), 7.37-7.31 (m, 2H), 7.29-7.25 (m, 2H), 6.80 (d, J=8.6 Hz, 1H), 6.62 (d, J=8.6 Hz, 1H), 4.26 (t, J=6.1 Hz, 1H), 3.96 (s, 2H), 3.89 (s, 3H), 3.86 (s, 3H), 3.75 (s, 3H), 3.67 (d, J=6.3 Hz, 2H). $^{13}$C NMR (101 MHz, CDCl$_3$) δ 191.1, 152.6, 151.8, 147.8, 145.6, 142.4, 141.0, 134.8, 128.8, 127.6, 127.3, 127.0, 126.0, 124.7, 124.4, 119.8, 107.1, 60.7, 60.6, 55.9, 46.8, 35.9, 32.5. HRMS (ESI) calcd for C$_{31}$H$_{28}$O$_4$S [M+H]$^+$: 497.1781, found: 497.1732.

Synthesis of TE40

TE40 was synthesized by the reaction scheme:

3H) 3.8 (s, 3H). $^{13}$C NMR (101 MHz, CDCl$_3$) δ ppm 168.2, 139.0, 130.2, 127.9, 123.9, 122.8, 121.3, 108.8, 102.6, 51.7, 32.9.

At a temperature of 0° C., a round bottom flask was charged with cyclohexanecarbonyl chloride (465 mg, 3.17 mmol), DCM (15 mL), AlCl$_3$ (423 mg, 3.17 mmol) and magnetic stir bar. The reaction mixture was allowed to stir and come to rt. Indole 9 (200 mg, 1.06 mmol) was added as a DCM (6 mL) solution over the course of 25 min. The reaction mixture was then stirred for 18 h. The reaction was quenched with saturated NH$_4$Cl, extracted with DCM, dried with Na$_2$SO$_4$, solvent removed under reduced pressure and purified using flash column chromatography. The ester intermediate was hydrolyzed in 2 M NaOH in refluxing MeOH for 4 h. The reaction mixture was cooled, acidified with 1 M HCl and allowed to solidify upon standing. The carboxylic acid product was collected by vacuum filtration and used without further purification. $^1$H NMR (400 MHz, DMSO-d$_6$) δ 12.60 (br. s., 1H), 8.90 (s, 1H), 8.48 (s, 1H), 7.87 (dd, J=1.4, 8.8 Hz, 1H), 7.58 (d, J=9.0 Hz, 1H), 3.88 (s, 3H), 3.11 (t, J=10.3 Hz, 1H), 1.78 (t, J=11.5 Hz, 4H), 1.68 (d, J=12.1 Hz, 1H), 1.52-1.30 (m, 4H), 1.26-1.14 (m, 1H). $^{13}$C NMR (101 MHz, DMSO-d$_6$) δ 198.4, 168.1, 139.7, 138.7, 125.7, 124.4, 124.1, 123.9, 114.7, 110.4, 46.4, 33.3, 29.6, 25.6, 25.4.

The carboxylic acid intermediate was transformed into TE40 as previously reported in ACS Chem Biol 2011, 6, 724-732. The three synthetic steps gave TE40 with a 62% overall yield. $^1$H NMR (500 MHz, CDCl$_3$) δ 9.09 (d, J=1.5 Hz, 1H), 7.92 (dd, J=1.7, 8.6 Hz, 1H), 7.80 (d, J=7.3 Hz,

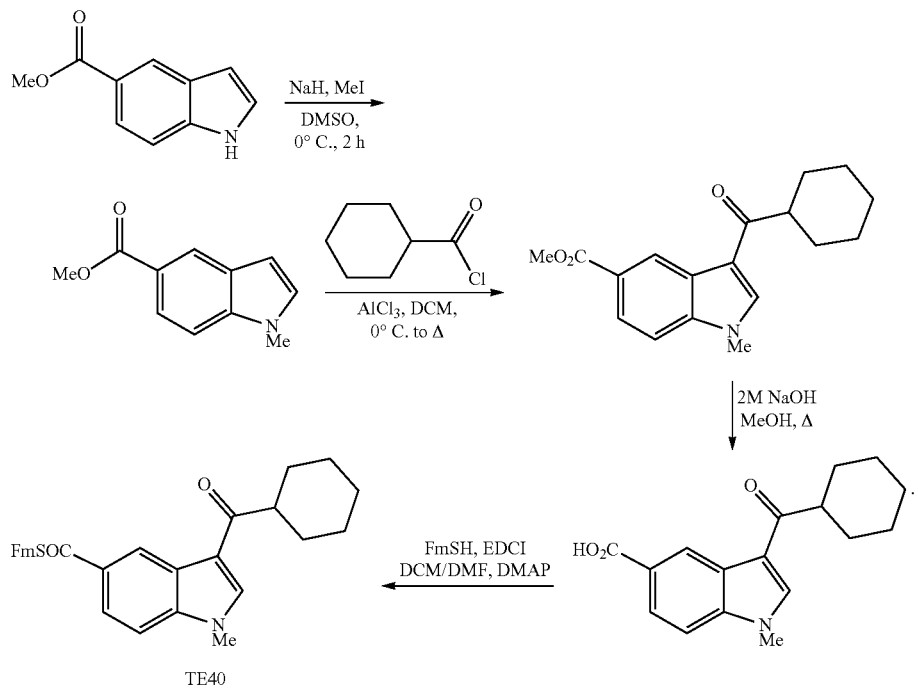

Methyl 1-methyl-1H-indole-5-carboxylate was prepared according to the article, Org. Lett. 2014, 16, 1124-1127, which is hereby incorporated by reference in its entirety. R$_f$=0.49 in hexanes:EtOAc=2:1. $^1$H NMR (400 MHz, CDCl$_3$) δ ppm 8.4 (s, 1H) 7.9 (d, J=8.6 Hz, 1H) 7.3 (d, J=9.4 Hz, 1H) 7.1 (d, J=3.1 Hz, 1H) 6.6 (d, J=3.9 Hz, 1H) 3.9 (s, 2H), 7.78-7.75 (m, 3H), 7.42-7.38 (m, 2H), 7.37-7.31 (m, 3H), 4.27 (t, J=6.4 Hz, 1H), 3.85 (s, 3H), 3.68 (d, J=6.4 Hz, 2H), 3.00 (tt, J=3.0, 11.7 Hz, 1H), 1.96-1.85 (m, 4H), 1.77 (d, J=12.2 Hz, 1H), 1.68-1.58 (m, 2H), 1.46-1.35 (m, 2H), 1.35-1.28 (m, 1H). $^{13}$C NMR (126 MHz, CDCl$_3$) δ 199.2, 191.7, 145.8, 140.9, 140.1, 136.2, 131.8, 127.6, 127.1, 126.0, 124.8, 123.5, 122.2, 119.8, 116.5, 109.6, 48.0, 47.0, 33.7, 32.8, 29.8, 26.0, 25.9. HRMS (ESI) calcd for $C_{31}H_{29}NO_2S$ [M+H]$^+$: 480.1992, found: 480.1980.

Synthesis of TE42

TE42 was synthesized by the reaction scheme:

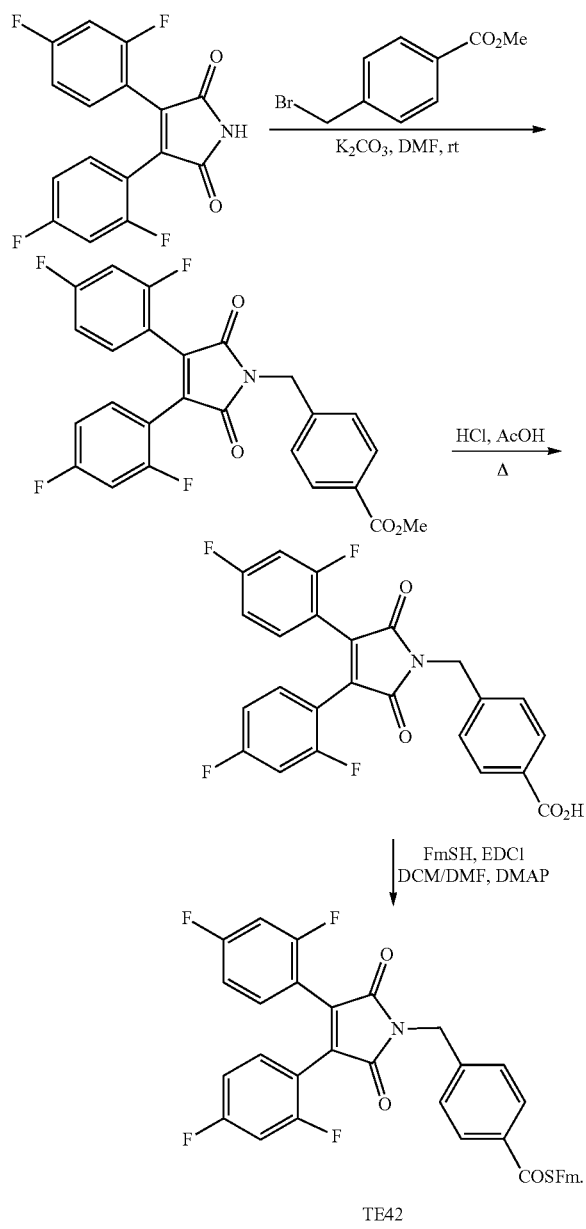

The starting material 3,4-bis(2,4-difluorophenyl)-1H-pyrrole-2,5-dione, was prepared according to the article, Nacheva, K. et al. Fluorescent properties and resonance energy transfer of 3,4-bis(2,4-difluorophenyl)-maleimide. *Org. Biomol. Chem.* 10, 7840-7846 (2012), which is hereby incorporated by reference in its entirety.

A round bottom flask was charged with starting material 3,4-bis(2,4-difluorophenyl)-1H-pyrrole-2,5-dione (250 mg, 0.78 mmol), methyl 4-(bromomethyl)benzoate (179 mg, 0.78 mmol), $K_2CO_3$ (215 mg, 1.56 mmol), DMF (8 mL), a magnetic stir bar and stirred at rt for 12 h. The reaction was quenched with water, extracted with EtOAc, washed with brine, dried with $Na_2SO_4$, solvent removed under reduced pressure and purified using flash column chromatography. The ester was hydrolyzed using HCl/AcOH (1:1, 6 mL) under reflux conditions. The product was filtered and washed with water to neutrality and used without further purification. $^1$H NMR (500 MHz, DMSO-d$_6$) δ 12.94 (br. s., 1H), 7.93 (d, J=8.3 Hz, 2H), 7.60-7.54 (m, 2H), 7.49 (d, J=7.8 Hz, 2H), 7.38-7.31 (m, 2H), 7.23 (dt, J=2.0, 8.6 Hz, 2H), 4.83 (s, 2H). $^{13}$C NMR (126 MHz, DMSO-d$_6$) δ 168.7, 167.0, 162.6 (dd, J=252, 14 Hz), 160.6 (dd, J=253, 14 Hz), 141.3, 133.5, 133.0 (d, J=5 Hz), 130.0, 129.6, 127.6, 113.5 (d, J=15 Hz), 112.0 (d, J=23 Hz), 104.7 (t, J=26 Hz), 41.4.

The carboxylic acid intermediate was transformed into TE42 as previously reported in as previously reported in ACS Chem Biol 2011, 6, 724-732. The four synthetic steps gave TE42 with a 72% overall yield. $^1$H NMR (500 MHz, CDCl$_3$) δ7.92 (d, J=8.3 Hz, 2H), 7.76 (d, J=7.8 Hz, 2H), 7.72 (d, J=7.3 Hz, 2H), 7.54-7.47 (m, 4H), 7.43-7.37 (m, 2H), 7.36-7.30 (m, 2H), 7.01-6.94 (m, 2H), 6.84-6.78 (m, 2H), 4.85 (s, 2H), 4.26 (t, J=6.1 Hz, 1H), 3.68 (d, J=5.9 Hz, 2H). $^{13}$C NMR (101 MHz, CDCl$_3$) δ 191.0, 169.0, 163.8 (dd, J=254, 12 Hz), 161.1 (dd, J=258, 14 Hz), 145.5, 141.2, 141.0, 136.7, 133.3, 132.4 (dd, J=10, 5 Hz), 128.9, 127.73, 127.69, 127.1, 124.7, 119.9, 112.0 (dd, J=22, 4 Hz), 111.8, 104.7 (t, J=25 Hz), 46.7, 41.9, 32.6. HRMS (ESI) calcd for $C_{38}H_{23}F_4NO_3S$ [M+H]$^+$: 650.1408, found: 650.1425.

General Procedure for the Amidation Reaction Between Thio Esters and Sulfonyl Azides The amidation reaction between the thio esters and the sulfonyl azides is shown below:

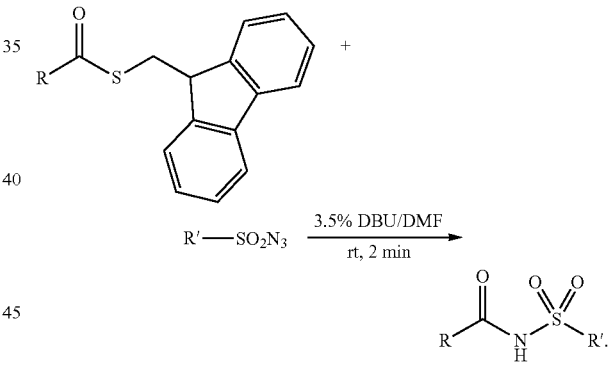

N-acyl sulfonamides was prepared according to the article, Chem Comm 2012, 48, 1526-1528, which is hereby incorporated by reference in its entirey. All the reactions were performed at 20-30 mg scale. The 9-flourenylmethyl thioester was taken in a 1.5 mL eppendorf and 3.5% DBU/dry DMF solution was added (per 1 µmol of thioester, 4.7 µL of 3.5% DBU/dry DMF solution was added) and the reaction was stirred for a minute. Then the sulfonylazide (1 eq to thioester) was added to the reaction mixture and immediately bubbling was observed. After the reaction was completed in a minute, (monitored by LC-MS) water (200 µL) was added and the pH was adjusted to 7.0 using 1M HCl solution. The reaction mixture was extracted with DCM until there is no product in the aqueous layer (checked by TLC or LC-MS). The product was purified by flash chromatography.

SZ11TA40

$^1$H NMR (500 MHz, DMSO-d$_6$) δ 12.72-12.57 (m, 1H), 8.86 (s, 1H), 8.52 (s, 1H), 8.08 (d, J=8.8 Hz, 2H), 7.89 (d,

J=8.8 Hz, 2H), 7.77 (dd, J=1.5, 8.8 Hz, 1H), 7.66 (d, J=8.3 Hz, 2H), 7.60 (d, J=8.8 Hz, 1H), 7.50 (d, J=8.3 Hz, 2H), 3.88 (s, 3H), 3.19-3.10 (m, 1H), 1.78 (t, J=12.2 Hz, 4H), 1.69 (d, J=12.2 Hz, 1H), 1.51-1.34 (m, 5H), 1.30 (s, 9H). $^{13}$C NMR (126 MHz, DMSO-$d_6$) δ 198.4, 166.4, 151.2, 144.7, 139.7, 139.0, 138.5, 135.6, 128.3, 126.9, 126.8, 125.9, 125.6, 125.4, 123.4, 123.1, 114.8, 110.6, 46.4, 34.3, 33.3, 31.0, 29.6, 25.6, 25.3. HRMS (ESI) calcd for $C_{33}H_{36}N_2O_4S$ [M+H]$^+$: 557.2469, found: 557.248.

SZ12TA42

$^1$H NMR (500 MHz, DMSO-$d_6$) δ 7.89-7.84 (m, 4H), 7.56 (dt, J=6.6, 8.4 Hz, 2H), 7.48 (d, J=8.3 Hz, 2H), 7.39-7.32 (m, 6H), 7.31-7.28 (m, 1H), 7.22 (dt, J=2.5, 8.6 Hz, 2H), 7.07 (t, J=6.1 Hz, 1H), 6.97 (td, J=1.2, 7.8 Hz, 1H), 4.79 (s, 2H), 4.42 (d, J=6.4 Hz, 2H). $^{13}$C NMR (126 MHz, DMSO-$d_6$) δ 168.7, 167.3, 162.6 (dd, J=251, 13 Hz), 160.0 (dd, J=254, 13 Hz), 149.5, 148.8, 143.2, 141.6, 139.8, 133.5, 133.0 (dd, J=11, 4 Hz), 130.0, 128.7, 127.5, 127.1, 127.0, 118.3, 113.4 (dd, J=16, 2 Hz), 112.1 (dd, J=22, 3 Hz), 110.2, 109.56, 105.7, 104.7 (t, J=26 Hz), 45.9, 41.4. HRMS (ESI) calcd for $C_{37}H_{24}F_4N_4O_7S$ [M+H]$^+$: 745.1375, found: 745.141.

SZ35TA24

$^1$H NMR (400 MHz, DMSO-$d_6$) δ 8.04-8.00 (m, 2H), 7.85 (d, J=8.6 Hz, 2H), 7.80 (d, J=8.6 Hz, 2H), 7.77-7.73 (m, 2H), 7.46-7.39 (m, 2H), 7.24 (d, J=8.2 Hz, 2H), 7.21-7.16 (m, 1H), 7.12-7.07 (m, 4H), 6.86 (d, J=8.6 Hz, 1H), 6.72 (d, J=8.6 Hz, 1H), 3.88 (s, 2H), 3.75 (s, 3H), 3.71 (s, 3H), 3.61 (s, 3H). $^{13}$C NMR (101 MHz, DMSO-$d_6$) δ 166.0, 157.4, 156.1, 152.3, 151.2, 146.7, 143.7, 141.9, 139.1, 133.5, 130.4, 130.2, 128.8, 128.5, 128.5, 128.2, 126.7, 125.9, 124.5, 123.9, 119.2, 118.7, 107.8, 60.4, 60.2, 55.8, 35.2. HRMS (ESI) calcd for $C_{35}H_{31}NO_7S$ [M+H]$^+$: 610.1894, found: 610.1911.

SZ10TA2

$^1$H NMR (500 MHz, DMSO-$d_6$) δ12.00 (br. s., 1H), 7.94 (d, J=8.8 Hz, 2H), 7.80 (d, J=8.3 Hz, 2H), 7.75 (d, J=8.8 Hz, 2H), 7.60 (d, J=8.3 Hz, 2H), 7.57 (d, J=8.3 Hz, 2H), 7.36-7.30 (m, 2H), 7.20-7.13 (m, 4H), 7.07-7.00 (m, 1H), 6.90 (d, J=8.8 Hz, 2H), 3.70 (s, 2H), 3.67 (br. s., 2H), 3.34-3.27 (m, 4H), 3.19-3.12 (m, 2H), 2.64-2.57 (m, 2H), 1.37-1.31 (m, 4H), 0.92 (s, 6H). $^{13}$C NMR (126 MHz, DMSO-$d_6$) δ 164.7, 153.6, 145.0, 143.2, 142.8, 138.8, 135.9, 130.3, 129.0, 128.9, 128.6, 127.7, 127.6, 125.7, 125.4, 118.9, 112.7, 56.9, 56.8, 51.8, 43.3, 37.4, 29.2, 28.5, 27.6. FIRMS (ESI) calcd for $C_{36}H_{42}N_4O_5S_3$ [M+H]$^+$: 707.2390, found: 707.2403.

ALAS Activity

ALAS activity was determined according to the article, Stojanvoski, B. M., Breydo, L., Hunter, G. A., Uversky, V. N, Ferreira G. C. (2014) *Biochim. Biophys. Acta* 1844, 2145-2154, which is hereby incorporated by reference in its entirety. The results are shown in Table 1.

TABLE 1

| ALAS activity | | |
|---|---|---|
| TA/SZ-containing Compounds | Compounds | IC50 (μM) |
| TA40-containing compounds | SZ10TA40 | 8.6 ± 0.9 |
| | SZ11TA40 | 19.3 ± 2.7 |
| | SZ17TA40 | TGS hits, but low ALAS inhibition |
| | SZ14TA40 | Not a TGS hit |
| | SZ31TA40 | Not a TGS hit |

TABLE 1-continued

| ALAS activity | | |
|---|---|---|
| TA/SZ-containing Compounds | Compounds | IC50 (μM) |
| TA42-containing compounds | SZ12TA42 | 8.6 ± 0.9 |
| | SZ27TA42 | TGS hits, but low ALAS inhibition |
| | SZ14TA42 | Not a TGS hit |
| | SZ35TA24 | 31.4 ± 1.8 |
| TA24-containing compounds | SZ15TA42 | TGS hits, but low ALAS inhibition |
| SZ10-containing compounds | SZ10TA2 | 43.0 ± 5.8 |
| | SZ10TA15 | Not a TGS hit |
| | SZ10TA20 | Not a TGS hit |
| | SZ10TA21 | Not a TGS hit |
| | SZ10TA25 | Not a TGS hit |
| | SZ10TA34 | Not a TGS hit |
| | SZ17TA7 | 50.0 ± 6.1 |

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility. It is therefore intended by the appended claims to cover any and all such applications, modifications and embodiments within the scope of the present invention.

As used herein, the singular forms "a," "an" and "the" are intended to include the plural forms as well, unless the context clearly indicates otherwise. Furthermore, to the extent that the terms "including," "includes," "having," "has," "with" or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of," "consists essentially of," "consisting" and "consists" can be used interchangeably.

All patents, patent applications, provisional applications, and publications referred to or cited herein are incorporated by reference in their entirety, including all figures and tables, to the extent they are not inconsistent with the explicit teachings of this specification.

REFERENCES

1. Fratz, E. J., Stojanvoski, B. M., and Ferreira, G C. (2013) In *Handbook of Porphyrin Science* (Ferreira, G. C., Kadish, K. M. Smith, K. M. and Guilard, R., Eds.), pp 3-68, World Scientific Publishing Co.
2. Zoubida, K., Goya, L., Deybach, J.-C., and Puy, H. (2013) In *Handbook of Porphyrin Science* (Ferreira, G. C., Kadish, K. M. Smith, K. M. and Guilard, R., Eds.), pp 89-118, World Scientific Publishing Co.
3. Matthew, M. and Neuberger, A. (1963) *Biochem. J.* 87, 601-612.
4. Sharpless, K. B. and Manetsch, R. (2006) *Expert Opin. Drug Discov.* 1, 525-538.
5. Hu, X., Sun, J., Wang, H. G., and Manetsch, R. (2008) *J. Am. Chem. Soc.* 130, 13820-13821.

Hu, X. and Manetsch, R. (2010) *Chem. Soc. Rev.* 39, 1316-1324.

Stojanovski, B. M., Breydo, L., Hunter, G. A., Uversky, V. N, Ferreira G. C. (2014) *Biochim. Biophys. Acta* 1844, 2145-2154.

We claim:
1. A method of treating *porphyria*, the method comprising administering to a subject an effective amount of a composition comprising one or more compounds of Formulas (I-V):

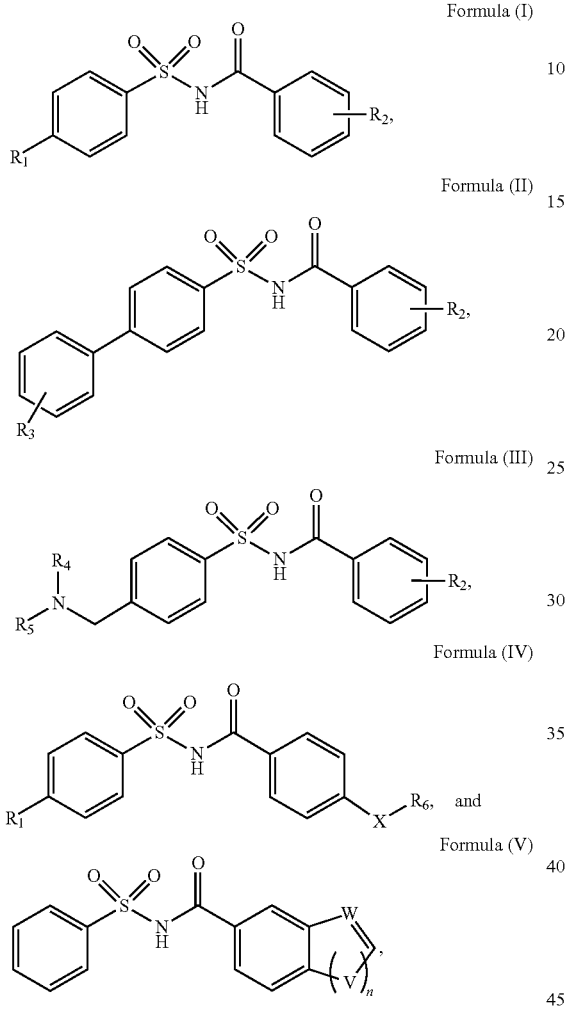

Formula (I)

Formula (II)

Formula (III)

Formula (IV)

Formula (V)

wherein $R_1$, $R_2$, $R_3$, $R_4$, $R_5$, $R_6$ are independently selected from the group consisting of: H; F; Cl; Br; I; OH; $C_{1-14}$ linear, branched, or cyclic alkyl; $C_{2-14}$ linear, branched, or cyclic alkenyl; $C_{2-14}$ linear, branched, or cyclic alkynyl —OR, where R is $C_{1-14}$ alkyl or $C_{2-14}$ alkenyl; $C_{6-14}$ aryl; $C_{7-28}$ aralkyl; $C_{7-28}$ alkaryl; heteroaryl, halogenated alkyl; heterocyclyl; amino; alkylamino; arylamino; dialkylamino, where the alkyls are independently $C_{1-14}$ alkyl; alkylarylamino; diarylamino; tetraalkylammonium, where the alkyls are independently $C_{1-14}$ alkyl; aryltrialkylammonium, where the alkyls are independently $C_{1-14}$ alkyl; diaryldialkylammonium, where the alkyls are independently $C_{1-14}$ alkyl and the aryls are independently $C_{6-14}$ aryl; acylamino; hydroxyl; alkoxy; aryloxy; arylalkoxy; acyloxy; nitro; carbamoyl; trifluoromethyl; phenoxy; benzyloxy; alkaryl; arylalkyl; carbamate; hydroxyalkyl; aminoalkyl; alkoxyalkyl; hydroxyalkyl; aminoalkyl; alkoxyalkyl; alkyltriphenylphosphonium; —C(O)R, where R is $C_{1-14}$ alkyl or $C_{2-14}$ alkenyl; —C(O)H; —C(O)OH; —OC(O)R where R is $C_{1-14}$ alkyl or $C_{2-14}$ alkenyl; —ROC(O)R' where R and R' are independently $C_{1-14}$ alkyl or $C_{2-14}$ alkenyl; —RC(O)OR', where R is $C_{1-14}$ alkylene, $C_{2-14}$ alkenylene, or arylene and R' is $C_{1-14}$ alkyl, $C_{2-14}$ alkenyl, or aryl; —C(O)OR where R is $C_{1-14}$ alkyl, $C_{2-14}$ alkenyl, or aryl; —OCOOR, where R is $C_{1-14}$ alkyl, $C_{2-14}$ alkenyl, or aryl; —C(O)NRR' where R and R' are independently H, $C_{1-14}$ alkyl, $C_{2-14}$ alkenyl, or aryl; —N(R)C(O)R', where R is $C_{1-14}$ alkyl, $C_{2-14}$ alkenyl, or aryl; —N(C(O)R)(C(O)R'), where R and R' are independently $C_{1-14}$ alkyl, $C_{2-14}$ alkenyl, or aryl or R and R' are combined as $C_{1-14}$ alkylene, $C_{2-14}$ alkenylene, or arylene; —OCN; —NCO; —ONO$_2$; —CN; —NC; —NO; —CH=NOH; —B(OH)$_2$; —B(OR)(R'), where R where R and R' are independently H, $C_{1-14}$ alkyl, or $C_{2-14}$ alkenyl; —B(OR)(OR'), are independently H, $C_{1-14}$ alkyl, or $C_{2-14}$ alkenyl; —PR$_2$, where R is independently selected from H, $C_{1-14}$ alkyl, or $C_{2-14}$ alkenyl; —OP(O)(OR)$_2$, where R is independently selected from H, $C_{1-14}$ alkyl, or $C_{2-14}$ alkenyl; —P(O)(R)(OH), where R is selected from $C_{1-14}$ alkyl or $C_{2-14}$ alkenyl; —SH; thioalkyl; —SR, where R is selected from $C_{1-14}$ alkyl or $C_{2-14}$ alkenyl; —SSR, where R is $C_{1-14}$ alkyl or $C_{2-14}$ alkenyl; sulfonamide; —S(O)R, where R is $C_{1-14}$ alkyl or $C_{2-14}$ alkenyl; —SO$_2$H; —SO$_3$H; thiocyanate; isothiocyanate; —C(S)R where R is $C_{1-14}$ alkyl or $C_{2-14}$ alkenyl; where X is O, N, or S; where V is —CH$_2$—, CO, S, and NR$_7$, where R$_7$ is independently H; $C_{1-14}$ alkyl; $C_{2-14}$ alkenyl; heteroalkyl; or heteroaryl;

wherein n is an integer from 1 to 4; and wherein W is —CH$_2$—, O, S and NR$_8$, where R$_8$ is selected from H, methyl, ethyl, n-propyl, isopropyl, n-butyl, sec-butyl, isobutyl, tert-butyl; ethenyl, propenyl, butenyl, where the double bond can be located at any position in the alkenyl carbon chain, including any alkenyl conformational isomers; heteroalkyl; and heteroaryl.

2. The method of treating *porphyria* of claim 1, wherein the compound is selected from the group consisting of:

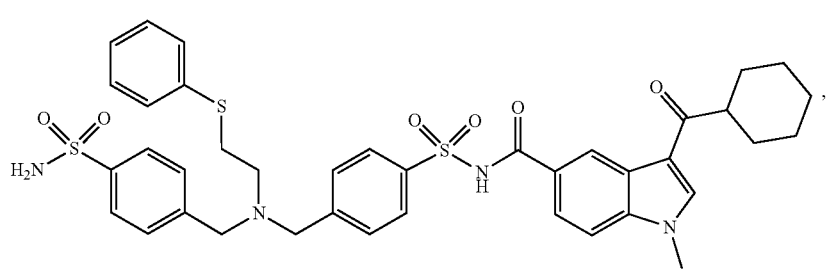

-continued

SZ11TA40

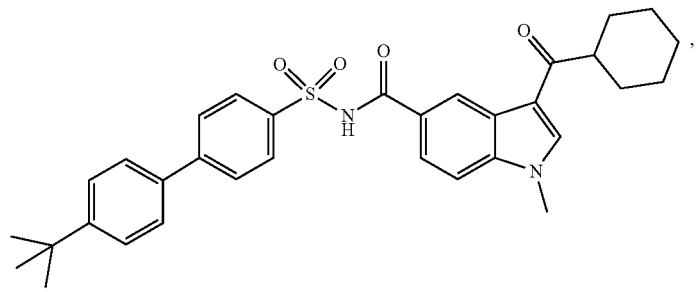

SZ12TA42

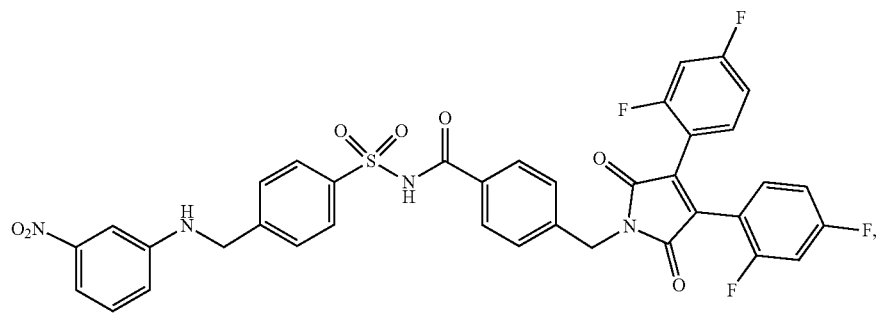

SZ35TA24

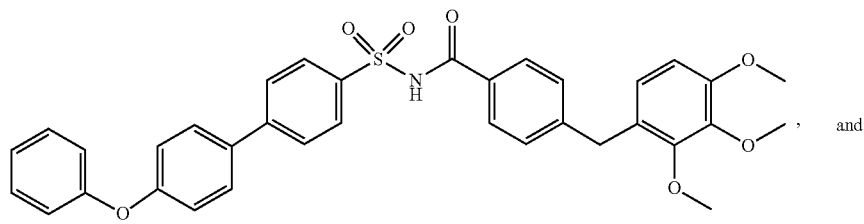

and

SZ10TA2

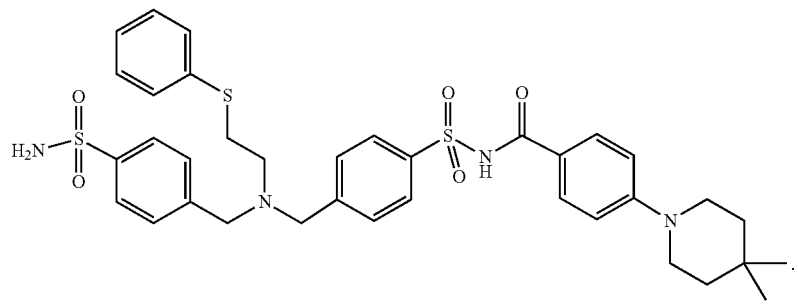

3. The method of treating *porphyria* of claim 1, wherein the administering comprises:
   oral administration of a capsule, tablet, granule, spray, or syrup;
   non-oral administration of an aqueous suspension or an oily preparation as a drip, suppository, salve, or ointment;
   injection;
   subcutaneously;
   intraperitoneally;
   intravenously;
   intramuscularly;
   intradermally;
   intraocularly;
   intranasally; or
   intra-auricularly.

4. The method of treating *porphyria* of claim 1, wherein the administering is by a controlled released formulation, a depot formulation, or an infusion pump delivery and through at least one of intraocular, intranasal, and intra-auricular pathways.

* * * * *